United States Patent [19]

Duret et al.

[11] Patent Number: 4,952,149
[45] Date of Patent: Aug. 28, 1990

[54] PROCESS AND APPARATUS FOR TAKING A MEDICAL CAST

[75] Inventors: Francois Duret, Le Grand Lemps; Jean-Louis Blouin, Vienne, both of France

[73] Assignee: Hennson International, Vienne, France

[21] Appl. No.: 155,325

[22] Filed: Feb. 12, 1988

[30] Foreign Application Priority Data

Feb. 13, 1987 [FR] France .................... 87 02339

[51] Int. Cl.$^5$ .............................. A61C 5/00
[52] U.S. Cl. .................... 433/215; 433/229; 356/376
[58] Field of Search ............ 433/25, 215, 229, 213; 358/93; 128/665, 776, 777; 356/376

[56] References Cited

U.S. PATENT DOCUMENTS

| | | | |
|---|---|---|---|
| 3,665,097 | 5/1972 | Macovski | 358/93 |
| 4,184,175 | 1/1980 | Mullane, Jr. | 358/93 |
| 4,197,855 | 4/1980 | Lewin | 128/653 |
| 4,324,546 | 4/1982 | Heitlinger et al. | 433/213 X |
| 4,443,706 | 4/1984 | Di Matteo et al. | 356/376 X |
| 4,575,805 | 3/1986 | Moermann et al. | 128/776 X |
| 4,611,288 | 9/1986 | Duret et al. | 433/213 X |
| 4,657,394 | 4/1987 | Halioua | 356/376 |
| 4,742,237 | 5/1988 | Ozawa | 356/376 X |
| 4,837,732 | 6/1989 | Brandestiai et al. | 356/376 X |

Primary Examiner—Robert P. Swiatek
Assistant Examiner—Nicholas D. Lucchesi
Attorney, Agent, or Firm—Herbert Dubno; Andrew Wilford

[57] ABSTRACT

A method and apparatus for taking impressions of a portion of the body which utilizes the projection of a grid of sinusoidal profile onto the body portion of which the impression is to be taken. The projections are phase-shifted and resulting images are memorized and from the memorized images, the variations in intensity resulting from the phase-shift at each given point can be ascertained to enable the configuration of the region to be calculated.

32 Claims, 4 Drawing Sheets

PROCESS AND APPARATUS FOR TAKING A MEDICAL CAST

FIELD OF THE INVENTION

Our present invention relates to a process and to an apparatus for taking a medical cast.

BACKGROUND OF THE INVENTION

The field of application of this process encompasses the capture of the shapes of an implanting site of a dental prosthesis, whether fixed or mobile and of its environment in order to make a prosthesis, by the volume analysis for a diagnosis of part of the mouth, the capture of the shape of other parts of the body by the analysis of any part of the human body whose diagnostic and/or the associated therapy require its visualization as computerized images, and the capture of any shape with a view to making a prosthesis such as a hip, auricular, ocular, knee, finger and other joint prosthesis.

The capture of medical impressions are known to be made by means of a paste in dentistry, open surgical impression in the medical field, by micro-palpation, or by three-dimensional optical methods using, for example, ionizing radiations (photogrammetry, stereoscopy or interferential methods such as holography) or by the receipt of messages (NMR or ultrasound).

Methods of making an impression by means of pastes are time-consuming and require great skill from practitioner techniques such as photogrammetry and often are not sufficiently precise. Other techniques such as holography, are very complex and costly to implement, and sometimes provide performances which are better than may be strictly necessary for the particular object.

OBJECT OF THE INVENTION

The principal object of our invention is to overcome these disadvantages by providing a process for capturing a medical cast (impression), which is simple in concept and can obtain a three-dimensional image with good precision.

SUMMARY OF THE INVENTION

The invention provides a process which comprises:
projecting on a part of the body whose shape is to be captured, a grid of sinusoidal profile, then in repeating this projection at least twice, for a very brief time, with a phase shift between two successive projections equal in value to $2\pi/n$, where n is the number of projections;
effecting an optical reading of each projected image;
memorizing or storing each of these images and then correlating them, while observing the variations in intensity resulting from the variations of the phase shifts, at each point of the object; and
calculating the depth of each point in relation to a reference plane, the two other dimensions being defined, in relation to the optical system used, in the detector's plane.

The main advantage of this system is its great sensitivity which, for a z datum line corresponding to the depth, is of the order of P/100, where P is the pitch of the grid projected.

It is possible, therefore, to work with low spatial frequencies and hence with a minimum loss of contrast due to the transfer functions of the optics and of the objects whose form is to be captured.

Moreover, the measurement principle requires relatively simpler calculations than those necessary in the usual Moire techniques. Finally, this system is insensitive to the differences in reflectivity of the object and allows an unambiguous determination of the direction of the deformations (hollows or humps), which is particularly useful for taking dental casts.

According to a feature of the invention, the sinusoidal profile grid can be projected with a beam of parallel rays.

According to another embodiment of the invention, the sinusoidal profile grid can be projected as a divergent beam of rays with the reference plane perpendicular to an axis of projection.

Advantageously, this process consists of jointly using a complementary projection of a second system of fringes, in order to obtain a very precise phase difference with an indetermination of $2\pi$ with the first system, and a rough phase difference although without indetermination of $2\pi$ with the second system, and the correlation of the two results gives a very precise phase difference without indetermination of $2\pi$ at any point. In this case, the second system of fringes is provided by a single projection without any shift and, in this case, the calculation of the phase difference is carried out by a method of sub-sampling or a FOURIER method or any other equivalent method of phase analysis.

According to a preferred embodiment of the invention, this process consists of analyzing the variations of the coding phase deformed by the object in the two directions (x,y) defined in the plane of the detector, while taking into account the rate of modulation and the reflectivity of the object to produce a binary coded image of binary code value 1 if the phase exists and is continuous, and coded 0 if the phase does not exist or is discontinuous, then in considering the set of images thus obtained, in regrouping the images of the same value, and in defining their frontier by methods of dilation-erosion and of skeletization of the binary objects.

In order to obtain good precision of the measurement while using simple calculations, the number of projections of images of the grid on the part of the body to be observed is at least equal to three.

Moreover, this process consists of arranging, over the part of the body to be observed, a plurality of reference points visible in each of the positions of image acquisition, in carrying out several viewings at different angles, in detecting in each of the viewings the (x,y) position of each point, then through interpolation onto the relief, the z value of the latter, then by association of the physically identical reference points in gathering together the entire surface of each view into the same relief, the coordinates of which are defined in relation to a single image common reference code.

Advantageously, the process consists of calculating the position of each reference point in x or y of the image reflectivity, through the analysis of the histogram of the levels of grey, then in selecting the black spots of a suitable size, and finally in providing the center of gravity weighted by the levels of grey inside of these microspots.

It should be noted, that the reference points can be provided by characteristic points of the part of the body to be examined such as groove, cusp, face of the stump, streaks or points carried by objects laid on the body to be examined such as clamps in a dental application or even by reference points deposited by projections of ink or similarly, on the part of the body to be examined.

BRIEF DESCRIPTION OF THE DRAWING

The above objects, features and advantages of our invention will become more readily apparent from the following description, reference being made to the accompanying drawing in which.

SPECIFIC DESCRIPTION

Figure 1:
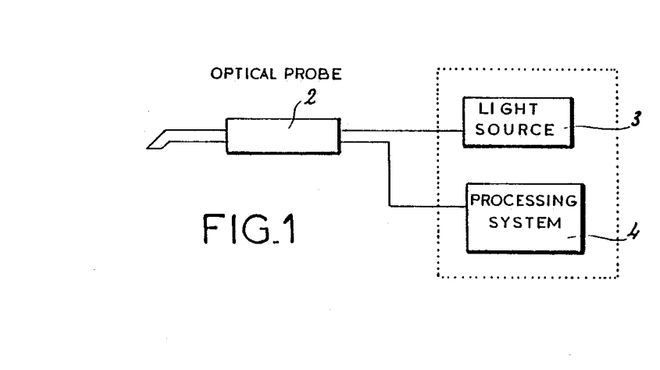
FIG. 1 is a general view, partially in block diagram form, of the main elements constituting this device.

As shown in FIG. 1, the device of the invention comprises an optical probe 2 connected, on the one hand, to a light source 3 and, on the other hand to a processing system 4.

The choice of the source conditions, in a large measure, the characteristics of the system, the source being chose, taking into account:
- an optimization of the emission spectrum of the source of the bandpass of the system,
- a power suitable to ensure a sufficient illumination of the detector as a function of the transmission of the system, and
- minimum overall measurements for a given power.

When the source cannot be placed in the probe for reasons of overall size, it is necessary to guide the light between the source and the probe, which may be done by means of an optical fiber. In this case, the light is collimated by means of coupling optics from the center of which the extremity of an optical fiber is seen under an angle $\alpha$, such that $\alpha$ is smaller or equal to P/4D, where P is the pitch of the grid and D is the maximum field depth corresponding to a correct modulation of the projected grid.

The wavelength of the projected light can be lower than 520πm, the light source emitting in a blue region of the ultraviolet, or the light source can be made of a solid-state device with a semiconductor of the laser diode type.

Figure 2:
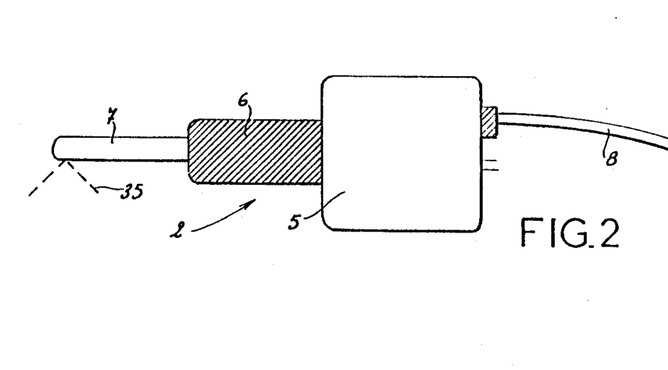
FIG. 2 is a diagrammatic view of the probe.

As shown in FIG. 2, the optical probe 2 appears in the shape of a casing of reduced dimensions comprising a body 5 as well as a part 6 suitable for holding in the hand of the practitioner, extended by a nosepiece 7 allowing for the coding projections and image retrieval. If the light source is formed by a laser diode or another component of the same type, it can be lodged in the body 5. In other cases, the light source is external and the light beam is guided through an optical fiber which may, for example, be associated with or may be in the cable 8, ensuring the transfer of the electronic signals between the probe proper and the processing system.

Figure 3:
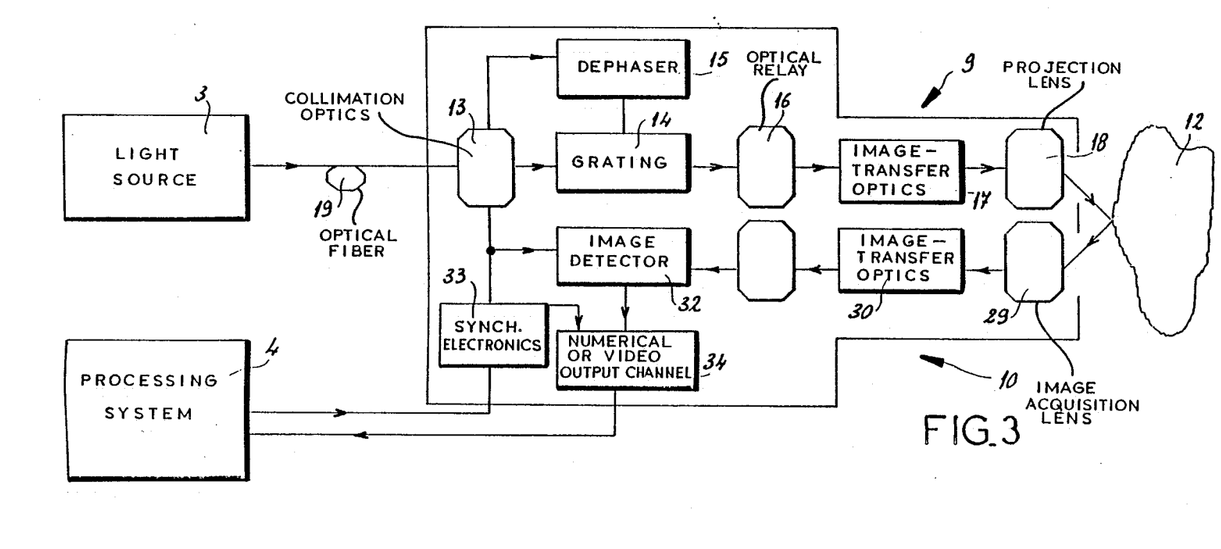
FIG. 3 is a block diagram of the main components forming the device.

The optical probe comprises a projection channel for the coding designated in FIG. 3 by the reference numeral 9, and one channel 10 for viewing the image, the object whose form is to be captured being defined on this same FIGURE by the reference numeral 12.

The projection channel of the coding comprises collimation optics 13, and a grating 14 fitted with its dephasing system 15, and an imaging optical system comprising an optical relay 16, an image transfer optics 17 and a projection lens 18. In this same FIGURE, the light source is designated by the reference 3, and the fiber for the transfer of the light beam bears the reference 19.

The principle of the method of profilometry by phase-coding assumes the creation of a coding of the sinusoidal type which is phase modulated. The creation of the coding comprises two coupled elements;
- the grating, and
- the phase modulator.

Figure 4:
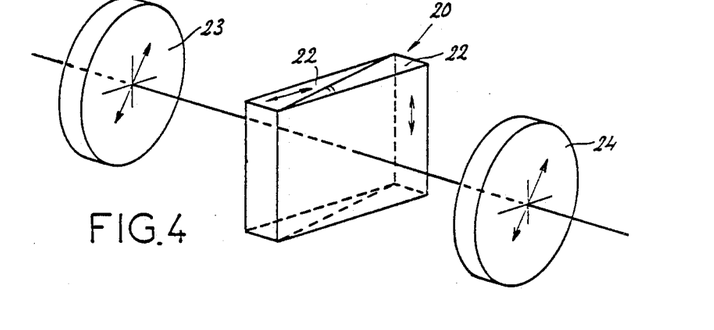
FIG. 4 is a highly diagrammatic view in perspective of a subassembly allowing the creation of a coding.

In the embodiment shown in FIG. 4, the transmission system comprises a Wollaston prism 20 formed by two similar wedges 22 cut in a birefringent material, for example, quartz, the fast and slow axes of which are opposed. This prism is illuminated by a monochromatic light beam, and placed between two polarizers 23 and 24, the axes of which are crossed or parallel and make a 45° angle with those of the prism, the value P of the pitch of the fringes created at the interface with the prism being given by the formula $$P = \frac{\lambda}{2\Delta n\, tg\theta}$$

where
- $\lambda$ is the wavelength of the light source,
- $\theta$ is the angle of each of the birefringent prisms forming the Wollaston prism, and
- $\Delta n$ is the difference between the ordinary and extraordinary indices of the material.

The fundamental advantage of this system is the complete compensation of the thermal and mechanical effects, since the beams follow the same path. The pitch of the grating is to be chosen as a function of the size of the object, of the magnification of the optical system and of the depth of the field D.

One of the advantages of the method of profilometry by phase analysis is that the uncertainty in z is of the order of P/100, which is advantageous for the precise study of small objects, for example, dental application, since we will recall that classical Moire or interferential processes only provide a precision lower than or equal to P/10.

For the application to the dental field, a ptich of the graying between 1 and 1.5 mm at the level of the reference plane can advantageously be selected.

The phase modulation corresponds in practice to M optical translations of the grating by a quantity nP/M, if M images are taken, where P is the pitch of the grating and n a whole number comprised between 0 and M, M being generally equal to 3 or 4 for ease of calculation.

These translations can be obtained by a mechanical shifting of the grating, by an optical process or by an electrooptic modulator.

Figure 5:
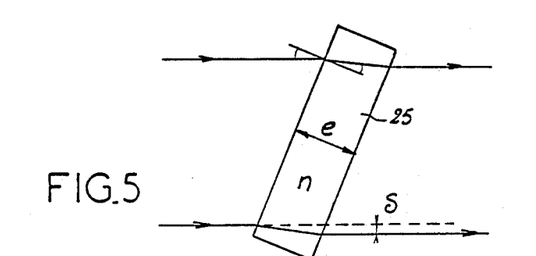
FIG. 5 is a side view of a phase modulation system.

By operating as shown in FIG. 5, by revolving a glass plate 25 of index n and of thickness e in a parallel beam, a lateral displacement of this beam of a value S is caused such that $$S = e^{\frac{\sin(i-r)}{\cos(r)}}$$

where i is the angle of incidence of the beam on the plate, and r is the refracted angle, these angles being linked together by the relationship $$\sin i = n \sin r$$

In polarized light, it is possible to use phase plates to create the desired modulation.

Figure 6:
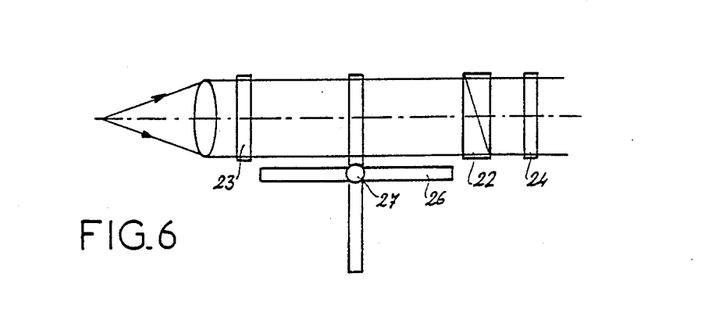
FIG. 6 is a side view of a first dephasing system.

As shown in FIG. 6, known dephasing plates 26 are successively introduced between the polarizer 23 and the Wollaston prism 22. A dephasing of the grating is thus created of a dephasing value of the phase plate. The different plates 26 can be mounted on a motorized wheel 27, the rotation of which is synchronized with the image acquisition.

Figure 7:
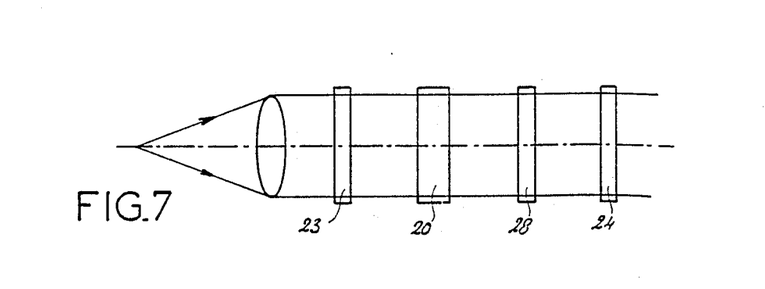
FIG. 7 is a side view of a second dephasing system.

According to another possibility, shown in FIG. 7, a quarter wave plate 28 is placed behind the Wollaston prism, its axis being parallel to the axis of the polarizer. By revolving the analyzer 24 by 108A, a dephasing value between 0 and $2\pi$ is obtained in a continuous manner.

The revolve the plates, it is possible to use a stepping motor, or a direct current motor. In the case of the stepping motor, the position of the blades is known by step counting from a 0 position.

The position can be determined by using a split disk presenting an opening which is perpendicular to it, and fixed on the shaft of the motor or of the wheel. A photodiode lights up the disk on one side and a photoelectric cell observes on the other side. When the hole or the slit passes in front of the photodiode, the cell is activated and emits a signal towards the processing system. In the case of a direct-current motor, it is preferable to mount a resistive potentiometer at the tip of the wheel's shaft, the measurement of the resistivity of the potentiometer permitting the position of the motor shaft to be known continuously. The set is controlled by electronic slaving which is situated in the processing system. The rotation of the plates is ensured either directly at the tip of the shaft, or by rack wheel or racked pulleys, this last solution being preferred in the case of a direct-current motor.

As shown in FIG. 3, the viewing channel comprises essentially an image acquisition lens 29, an image transfer system 30 and an image detector 32. The image detector is advantageously a detector of the C.C.D. type coupled to synchronization electronics 33 and to a numerical or video output channel 34.

Advantageously, the probe is so equipped as to be able to blow a compressed air jet 35 (FIG. 2) onto the object, in a direction parallel to the axis of projection and of observation. The purpose of this jet is to clean the observed surface from its impurities and, in the case of an endobuccal cast, it enables the gum to be pushed aside and to give access to deep zones, for example, at the level of the gum sulcus.

It is also advantageous to equip the probe with a device to prevent the formation of vapor. This device comprises means for heating to a temperature of at least 30° C., this means of heat operation when the probe is in the observation position or when it is in the resting position on its support.

These means of heating can be formed by a heating resistance supplied by a low-voltage current or by a film of hot air sent under low pressure.

In practice, the practitioner deposits, by means of a suitable marking pen, a few points on the tooth or on the stump or on any other area the relief of which has to be determined. After the introduction of the nosepiece of the probe into the patient's mouth, in the case of an endobuccal shape cast, direct viewing, without coding of the site to be examined is made.

The practitioner then positions the probe according to the viewing angle which seems most appropriate to him, then activates the acquisition of the first view. At this moment, the system synchronizes the acquisition of the images with the dephasing of the grating and, eventually, with the stroboscopy of the light source.

Once the images have been acquired, the practitioner can withdraw the probe and check his capture of the cast by selecting three types of information:

the image without coding of the area acquired,
three dimensional graphic representation of the calculated area, and
indicators of the quality of the relief corresponding to the precision of the measurement and a function of the response to coding.

After validation, this view serves as a reference for all of the subsequent views for which the practitioner proceeds according to the same principle along different angles. From the second acquisition of a view and of the detection of the reference points, the system can deliver on the screen a graphic image showing the reconstructed relief based on the correlated surfaces.

Figure 8:
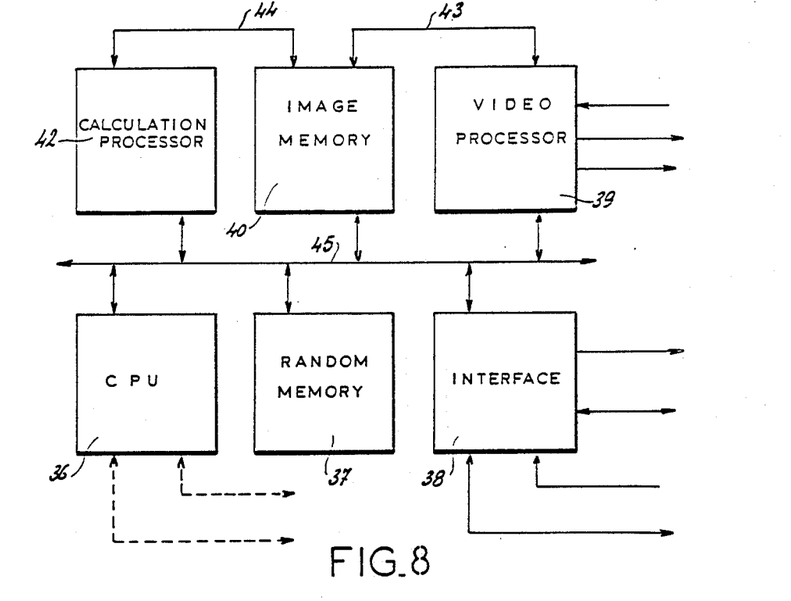
FIG. 8 is a block diagram showing the processing system.

As shown in FIG. 8, the calculator comprises six electronic modules linked by three buses, the modules being formed by a central unit card 36, a random calculation memory card 37, a specialized interface card 38, a card for processing the video signal 39, an image memory card 40 and a specialized calculation processing card 42, these modules being connected between one another by a digital video bus 43, a processing bus 44 and a systems bus 45.

Figure 9:
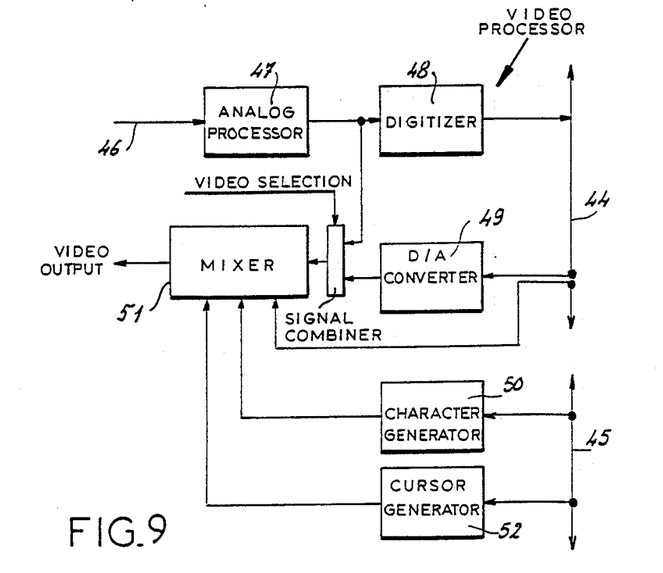
FIG. 9 is a view of a block diagram showing the video processing card.

FIG. 9 shows the card for processing the video signal serving as an interface between the camera set in the probe on the one hand, the viewing screen and the calculator on the other hand. This card receives at its input 46, an analog signal of the images originating from the probe which, on the one hand, is processed in 47 and injected into a digitizer 48 formed by an analog-digital converter over at least eight bits, this digitizer signal being then sent over the video bus and, on the other hand, sent to the viewing screen through a viewing module.

It should be noted that the card for the processing of the video signal receives, at its input, an image of at least eight bits digital signal originating from the video bus, which is injected after its passage in a conversion table programmable from the bus system into a digital-to-analog converter 49, and mixes (at mixer 51) this analog signal with, firstly, a graphic image originating from at least one graphic bit of the video bus, secondly alphanumeric (from character generator 50) originating from the bus system 45 and, thirdly, a cursor of any shape originating from a sub-module 52 generator of a cursor associated with a position control register.

The resulting signal is sent to the viewing screen, the image thus formed being decomposed into distinct parts or superimposed parts, namely:

a part representing one of the image memory planes or the image originating from the probe in which it appears, in overbrilliance or in different color, the state of the bit or bits originating from the planes of the selected graphic memories, a part which forms a display zone of alphanumeric text, and a cursor of any shape which can be activated and which can address any point of the screen.

Figure 10:
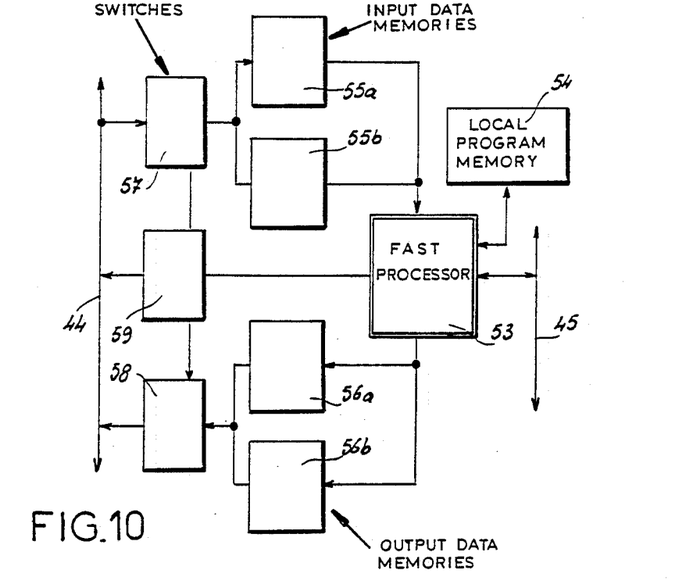
FIG. 10 is a block diagram showing the processing card.

FIG. 10 shows the processing card. This module enables quick processing of the images and is associated with local working memories which are of four types: programmed memories, input data memories, output data memories and internal registers.

In FIG. 10, the fast treatment processor is designated at 53, the local program memory at 54, the input data memories at 55a and 55b, the output data memories by reference numerals 56a and 56b, and the switches between the processing bus 44 and the input memories, the output memories and the fast treatment processor by reference numerals 57, 58 and 59. The processing card receives simultaneously at the input a flood of numerical data from at least two images originating through the processing bus 44 from image memory card 40, processes this flood of data, pixel for pixel, according to a program preloaded by the bus system 45 and delivers the results of the calculations in a digital form onto this processing bus 44.

Figure 11:
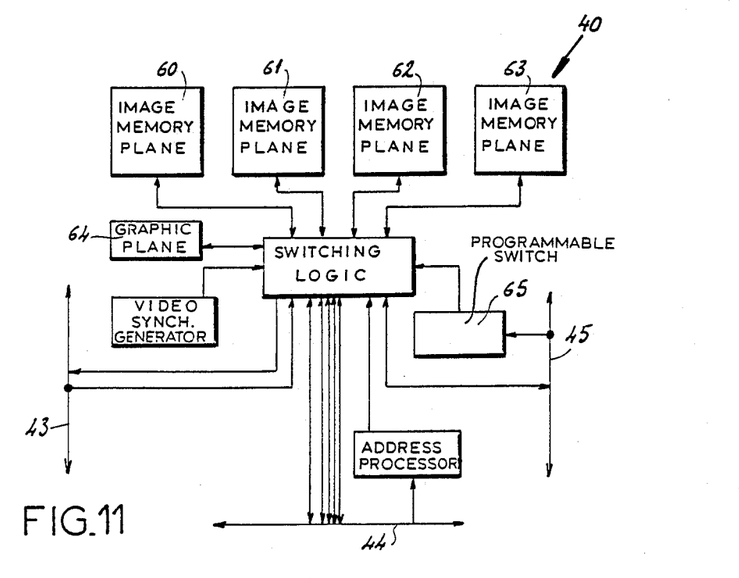
FIG. 11 is a block diagram showing the image memory card.

FIG. 11 shows the image memory card. This image memory card contains at least four digitized images of eight bits each, in the planes 60, 61, 62 and 63, and a graphic plane 64 of four bits and is provided with a sub-module 65 programmable by the bus system 45 which allows the images and graphic planes at the input or at the output to be multiplexed and switched towards the three bus system 45, video 43 and processor 44.

According to another characteristic of the invention, the specialized interfaces card 38 has electronic means available allowing synchronization of the acquisition of the images originating from the probe with the memory card and the means of driving the plates in rotation, these electronic means being triggered externally by the user.

Advantageously, the six electronic modules of the calculator are contained on the same card, the card being divided in six overlapping parts.

We claim:

1. A process for taking medical impressions, the process comprising the steps of:
   projecting onto part of a body whose impression is to be obtained a grid with a sinusoidal profile, and repeating this projection at least twice for a very brief period of time so as to generate projected grids with a phase shift between two successive projections of a value equal to $2\pi/n$ where n is the number of projections;
   reading an image projected optically for each projection with an optical system having a detector plane defined by a detector;
   memorizing each of said images;
   correlating the memorized images while observing variations in intensity resulting from variations of the phase shift for each of a multiplicity of points of said part of said body; and
   determining by calculation the depth of each of said points in relation to a reference plane, each of said points having two other dimensions defined in relation to the optical system used in the detector plane.

2. The process defined in claim 1 wherein the grid with a sinusoidal profile is projected by a cluster of parallel rays.

3. The process defined in claim 1 wherein the grid with a sinusoidal profile is projected by a beam of divergent rays along an axis of projection and the reference plane is perpendicular to the axis of projection.

4. The process defined in claim 1 wherein the projected grids form a first system of fringes, the process further comprising the steps of
   generating a complementary projection of a second system of fringes in order to obtain a very precise phase difference with an indetermination of $2\pi$ with the first system as one result, and a rough phase difference of $2\pi$ without indetermination with the second system as a second result, and
   correlating the two results to give a very precise phase difference of $2\pi$ at all points without indetermination.

5. The process defined in claim 4 wherein the second system of fringes is made by a single projection without any shift and the calculation of the phase difference is made by the Fourier method.

6. The process defined in claim 1, further comprising the steps of
   analyzing phase variations of a coding deformed by the part of the body in two directions defined in the plane of the detector,
   taking into account a rate of modulation and a reflectivity of the part of the body to produce a binary image coded 1 if a phase exists and is continuous and coded 0 if a phase does not exist or is discontinuous, and
   then, considering all of the images thus obtained, regrouping the images of the same value, and defining their border by methods of dilation-erosion and of skeletization of binary objects.

7. The process defined in claim 1 wherein the number of image projections of the grid onto the part of the body to be observed is at least 3.

8. The process defined in claim 1, further comprising the steps of
   inlaying on said part of said body a plurality of reference points visible in each of said images,
   reading several of said images at different angles,
   detecting in each of the images read the x and y coordinate of each point,
   interpolating on a relief a z coordinate of for said relief, and then
   defining a composite image of said part by coordinating to reference data.

9. The process defined in claim 8 further comprising the steps of
   calculating positions of reference points on said images by an analysis of a histogram of grey levels, then
   selecting black spots of a suitable size, and
   determining a center by weighting with the levels of grey.

10. The process defined in claim 9 wherein the reference points are provided by characteristic points of the part of the body to be examined, such as grooves, cusp, stump, face, scratches or points carried by objects added onto the body to be examined such as clamps, in the case of a dental application.

11. The process defined in claim 9 wherein the reference points are deposited by ink on the part of the body to be examined.

12. A device for taking medical impressions, the device comprising:
means including a light source for projecting onto part of a body whose impression is to be obtained a grid with a sinusoidal profile, and repeating this projection at least twice for a very brief period of time with a phase shift between two successive projections of a value equal to $2\pi/n$ where n is the number of projections;
means for reading an image projected optically for each projection with an optical system having a detector plane defined by a detector and including an optical probe and a processing system connected thereto;
means for memorizing each of said images;
means for correlating the memorized images while observing the variations in intensity resulting from the variations of the phase shift in each point of said part; and
means for determining by calculation the depth of each point in relation to a reference plane, the other two dimensions being defined, in relation to the optical system used, in the plane of the detector.

13. The device defined in claim 12 wherein the light source is distinct from the probe and the light is collimated by means of coupling optics from the center of which the extremity of an optical fiber is seen under an angle $\alpha$, such that $\alpha$ is smaller than or equal to P/4D, where
P is the pitch of the grid and
D is the maximum field depth corresponding to a correct modulation of the projected grid.

14. The device defined in claim 12 wherein the wavelength of the light projected is lower than 520μ and the light source emits in the blue or the ultraviolet.

15. The device defined in claim 12 wherein the light source is a solid-state device with a semiconductor of the laser diode type.

16. The device defined in claim 12 wherein the optical probe comprises a projection channel for coding and a viewing channel for reading the image.

17. The device defined in claim 16 wherein the projection channel for the coding comprises
collimation optics,
a grating fitted with a dephasing system, and
an optical imaging system comprising an optical relay, an image transfer optic and a projection lens.

18. The device defined in claim 17 wherein the grating comprises a Wollaston prism constituted by two similar wedges cut in a birefringent material illuminated by a monochromatic light wave and placed between two polarizers having axes which are crossed or parallel and which make a 45° angle with those of the prism, the value of the pitch p of the fringes created at the interface of the prism being given by the formula $$p = \lambda/2\Delta n \, tg\theta$$

where
$\lambda$ is the wavelength of the light source,
$\theta$ is the angle of each of the birefringent prisms forming the Wollaston prism, and
$\Delta n$ is the difference between the ordinary and extraordinary indices of the material.

19. The device defined in claim 17 wherein the dephasing system comprises
a motorized wheel comprising crystalline plates for dephasing and introduced sequentially or in synchronization with the shooting of the image.

20. The device defined in claim 19 wherein the plates are driven in rotation by a stepping motor, the position of the plates being known by counting the steps from a reference position determined by using a split or holed disk fitted on the wheel, the disk having one side fitted with a photodiode lighting the disk and another side fitted with a photoelectric cell which, when activated by the photodiode, emits a signal and feeds it to the processing system.

21. The device defined in claim 19 wherein the plates are rotated by a direct-current motor having control means comprising a resistive poteniometer, measurement of the resistivity of the potentiometer allowing the position of a shaft of the motor to be known continuously.

22. The device defined in claim 17 wherein the dephasing system includes
a quarter wave plate placed behind the Wollaston prism and having fast and slow axes at 45° to the axes of the prism, and
a rotatable analyzer allowing a dephasing value between 0 and $2\pi$ to be selected continually.

23. The device defined in claim 17 wherein the phase modulation system comprises
a glass plate of index n and of thickness e mounted pivotally to cause a lateral shift of the beam by a value S such that:

$$S = e\sin(i-r)/\cos(r)$$

where
i is the angle of incidence of the beam on the plate and
r is the refracted angle, the incidence and refracted angles being linked by the relation:

$$\sin i = n \sin r.$$

24. The device defined in claim 12 wherein the probe is fitted with a blowing system for projecting a compressed air jet onto the part of the body from an end of a nosepiece.

25. The device defined in claim 12 wherein the probe is equipped with a system avoiding the formation of vapor and comprising means for heating the probe to a temperature at least equal to 30° C., the heating means operating when the probe is in an observation position or when it is in a resting position on a holder.

26. The device defined in claim 12 wherein said processing system includes a calculator having six electronic modules linked by three buses, the modules being formed by
a central unit card,
a random-access memory for calculation,
a specialized interfaces card,
a video signal processing card,
an image memory card, and
a specialized processing card for calculation, these modules being linked to one another by a video-digital bus, a processing bus and a bus system.

27. The device defined in claim 26 wherein the processing card for the video signal serves as an interface between a camera arranged in the probe, a viewing screen and the calculator, said video signal processing card receiving at an input an analog signal of images originating from the probe and processing them and injecting them into the input of a digitizer formed by an analog-digital converter over at least eight bits forming a digitized signal that is then sent over the video bus and to the video screen through a viewing sub-module.

28. The device defined in claim 26 wherein the video signal processing card serves as an interface between a camera set in the probe and a viewing screen and the calculator, the video signal processing card receiving at an input a digital signal of eight bits originating from the video bus and injected after passing through a conversion table programmable from the bus system into a digital analog converter, and then processing this analog signal with, first, a graphic image originating from at least one graphic bit of the video bus, second, with alphanumeric characters originating from a sub-module allowing these said characters to be generated from the bus system and, third, with a cursor of any shape originating from the sub-module generating a cursor associated with a position control register and finally, sending the resulting signal to the viewing screen, the image thus formed on the screen being broken down into distinct parts:

one part representing an image memory plane or the image originating in the probe over which appears, in overbrilliance or in different colors, the state of the bit or bits originating from selected graphic memory planes, another part constituting a display zone of aliphanumeric text, and a cursor of any shape which may be activated and which can address may point of the screen.

29. The device defined in claim 26 wherein the specialized processing card receives simultaneously at its input a flow of digital data of at least two images originating through the processing bus from the image memory card, processes this flow of data, pixel by pixel, according to calculation programs preloaded by the bus system and delivers, over the same processing bus, the results of the calculations in digital form.

30. The device defined in claim 26 wherein the image memory card contains at least four digitized images of eight bits each, a graphic plane of four bits, and is provided with a sub-module programmable by means of the bus system to allow the digitized images and graphic planes to be multiplexed or switched either to the input or to the output of the bus, video and processor systems.

31. The device defined in claim 26 wherein the specialized interfaces card has electronic means for synchronizing the acquisition of the images originating from the probe with the memory card, and with electronic means for driving the plates in rotation, these electronic means being triggered externally by the user.

32. The device defined in claim 26 wherein the calculator comprises six electronic modules contained on the same card, the card being divided in six overlapping parts formed by a central unit,
a random-access memory for calculation,
a specialized interface,
video signal processing electronics,
an image memory, and
a specialized calculation processor, the parts being linked to one another by a video-digital bus, a processing bus and a bus system.

* * * * *